United States Patent [19]

Rajadhyaksha et al.

[11] 4,422,970
[45] Dec. 27, 1983

[54] METHOD OF SYNTHESIS OF 1-DODECYLAZACYCLOHEPTAN-2-ONE

[75] Inventors: Vithal J. Rajadhyaksha, Mission Viejo; James V. Peck, Costa Mesa; Gevork Minaskanian, Encino, all of Calif.

[73] Assignee: Nelson Research & Development Company, Irvine, Calif.

[21] Appl. No.: 380,162

[22] Filed: May 20, 1982

[51] Int. Cl.³ .............................................. C07D 223/10
[52] U.S. Cl. ............................. 260/239.3 R; 546/243; 548/543
[58] Field of Search ................. 260/239.3 R; 546/243; 548/543

[56] References Cited

PUBLICATIONS

Takahata et al., "Heterocycles" vol. 12, No. 11, pp. 1449–1451 (1979).

Primary Examiner—Robert T. Bond
Attorney, Agent, or Firm—Martin A. Voet

[57] ABSTRACT

In a method of synthesis of 1-substituted azacycloalkan-2-ones with primary alkyl halides and aralkyl halides as alkylating agents, the improvement comprising carrying out the N-alkylation in the presence of a phase transfer catalyst having the structural formula

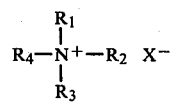

where X is suitable anion; and $R_1$, $R_2$, $R_3$ and $R_4$ are each alkyl or aralkyl groups having 1–18 carbon atoms, or $R_2$, $R_3$ and $R_4$ can form a part of a heterocyclic ring, with the proviso that the combined total of carbon atoms is between 16 and 40.

4 Claims, No Drawings

METHOD OF SYNTHESIS OF 1-DODECYLAZACYCLOHEPTAN-2-ONE

BACKGROUND OF THE INVENTION (1) Field of the Invention

The invention generally relates to an improved method of synthesis of 1-substituted azacycloalkan-2-ones and more particularly relates to an economic method of manufacturing high purity 1-dodecylazacycloheptan-2-one.

(2) Background of the Prior Art

The conventional method of preparing 1-alkyl substituted azacycloalkan-2-ones is based on the reaction of alkali salts of azacycloalkan-2-ones with alkylating agents; see, for example, L. Ruzicka, Helv. Chim. Acta 4, 472 (1921); C. S. Marvel et al., J. Org. Chem. 22, 1065 (1957); R. M. Moriarty, J. Org. Chem. 29, 2748 (1964); A. P. Swain, et al., J. Org. Chem. 18, 1087 (1953), and U.S. Pat. No.'s 3,989,815, 3,989,816, 3,991,203, and 4,112,170. In the prior art, the alkali salts of azacycloalkan-2-ones are prepared by reacting alkali metals or alkali metal hydrides with the corresponding lactams in the presence of an inert solvent under nitrogen atmosphere. This prior art method, however, is uneconomic because of the costly alkali metals or alkali metal hydrides, as well as large amounts of solvent required.

G. L. Isele et al., (Synthesis, 266, (1971)) disclose the alkylation of azacycloheptan-2-one with 1-bromobutane, benzyl chloride and 1-chlorooctadecane in the presence of dimethyl sulfoxide as the solvent and potassium hydroxide as the hydrogen halide acceptor. The authors attribute their results to a specific action of the dimethyl sulfoxide employed by them as solvent, namely to a marked promotion of the formation of the potassium salt of the lactam. In spite of its advantages when compared with older methods, this process is not suitable for commercial use on a large scale. Though the yields are adequate, the use of relatively costly potassium hydroxide, and the simultaneous use of large amounts of an expensive solvent are detrimental to its economy. Also removal of the solvent dimethyl sulfoxide from the product may pose problems if the boiling points are close.

In improving this method, U.S. Pat. No. 3,865,814 discloses that lactams, even in the absence of solvents, can be alkylated in high yields using primary alkyl or aralkyl halides and with alkali metal hydroxides as hydrogen halide acceptors. Specifically for economic reasons sodium hydroxide was preferred. However, this method requires repeated distillations and the fractions containing the product are contaminated with varying amounts of starting lactams. Thus, this method is not suitable from a commercial standpoint, especially where high purity of the alkylated lactam is essential for therapeutic applications.

During the past decade phase transfer catalysis has emerged as a technique for conducting useful synthetic reactions in heterogeneous reaction systems. Two classes of compounds are generally recognized as phase transfer catalysts: the quaternary "onium" salts and the polyethers. In the former category are found ammonium and phosphonium compounds and occasionally arsonium species as well. In the later group are found glymes, crowns, cryptands and related species. The two basic requirements of a phase transfer catalyst are that it be able to transfer one reactant from its normal phase into the normal phase of the second reactant and that the transferred reagent, once there, be available in a highly active form. Precisely how reactive the anion is depends upon the anion, the organic solvent in which the reaction is expected to occur, the amount of water present in the organic phase, the degree of association between cation and anion, concentration, temperature, and a number of other factors. Some of these factors are characteristic of the reaction or can be controlled in conventional ways but some are highly influenced by the choice of catalyst. Also, stability of the catalyst under the reaction conditions, availability of the catalyst, cost, ease of removal or recovery etc. are of importance in selection of a suitable catalyst.

J. Palacek et al., (Z. Chem., 17, 260 (1977)) disclose a method of manufacturing azacycloalkan-2-ones (5, 7 and 9 membered rings) with primary alkyl halides and aralkyl halides as alkylating agents using Benzyltriethylammonium chloride (BTEAC) as the phase transfer catalyst; however, the method produces low yields.

SUMMARY OF THE INVENTION

We have now discovered a substantially improved method of manufacture of 1-substituted azacycloalkan-2-ones which may be carried out economically, with high yields, by carrying out the N-alkylation in the presence of a defined class of phase transfer catalysts, namely, those catalysts having the structural formula

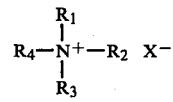

where X is a suitable anion such as a halide or a sulfate salt or other conventional anion such as, for example, Cl, Br, OH, $OSO_3H$, etc.; $R_1$, $R_2$, $R_3$ and $R_4$ are alkyl and aralkyl groups having 1–18 carbon atoms; with the proviso that the combined total of carbon atoms in $R_1$, $R_2$, $R_3$ and $R_4$ is between 16 and 40. Alternatively, $R_2$, $R_3$ and $R_4$ can form a part of a heterocyclic ring, such as pyridyl.

Preferred catalysts are those wherein $R_1$, $R_2$, $R_3$ and $R_4$ are symetrical, such as, for example, n-butyl, pentyl, etc. and where not more than two of the four alkyl groups have less than four carbon atoms.

The lipophilic catalysts covered by the above formula make the N-alkylation very facile by increasing substantially the hydroxide ion concentration in the organic phase.

DETAILED DESCRIPTION OF THE INVENTION

Referring more particularly to the foregoing formula, $R_1$, $R_2$, $R_3$ and $R_4$ are alkyl or aralkyl groups having 1–18 carbon atoms. Preferred substituents are butyl, heptyl, hexyl, octyl, decyl, dodecyl and benzyl.

Suitable phase transfer catalysts include quarternary ammonium salts, such as, for example, tricaprylylmethylammonium chloride (Aliquat 336®) trioctylmethylammonium bromide, tetrabutylammonium hydrogen sulfate (TBAHS), tetrabutylammonium chloride and bromide, tetraheptylammonium chloride (THAC) and bromide, didodecyldimethylammonium bromide, tetrahexyl- and tetrapentylammonium chloride and bromide, trioctylpropylammonium chloride or bromide, trioctylethylammonium chloride and bromide etc. The preferred catalysts are tricaprylylmethylammonium chloride (Aliquat 336®) and tetrabutylammonium hydrogen sulfate (TBAHS).

The amount of catalyst used may vary from about 0.01 to about 0.2 mole percent; 0.05 mole percent is preferred, though a higher mole percent of catalyst may be used to increase the reaction rate. The azacycloalkan-2-ones which can be used according to this invention are compounds of the following general formula:

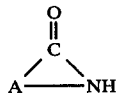

Where A is an aliphatic hydrocarbon chain consisting of 3 to 11 carbon atoms. This chain may carry one or more straight-chain or branched alkyl groups each with up to 4 carbon atoms as substituents. Examples of such azacycloalkan-2ones include azacyclopentan-2-one, azecyclohexan-2-one, azacycloheptan-2-one, azecyclooctan-2-one, azecyclononan-2-one, azacyclodecan-2-one, azacycloundecan-2-one, and azacyclododecan-2-one.

The alkylating agents which can be employed according to the present invention are compounds of the following general formula:

Where X is halogen and is preferably chlorine or bromine. R is hydrogen or a hydrocarbon moiety with 1 to 17 carbon atoms. This hydrocarbon moiety may consist of straight or branched aliphatic chains or of alicyclic or aromatic rings. It may contain all of these elements in any conbination and, moreover, olefinic double bonds. Examples of such organic halogen compounds are chloro- or bromo- derivatives of methane, ethane, propane, butane, pentane, hexane, heptane, octane, nonane, decane, undecane, dodecane, tridecane, tetradecane, pentadecane, hexadecane, heptadecane and octadecane. 1-substituted haloalkanes are preferred and specifically the ones where R—CH$_2$— represents dodecyl, tetradecyl, hexadecyl and octadecyl derivatives.

The molar ratio of alkylating agent to lactam may vary between about 1 and about 2. Since excess alkylating agent facilitates the reaction and is recovered unchanged by distillation at the end of the reaction and recycled, two moles of alkylating agent for each mole of lactam is preferred.

Suitable bases as hydrogen halide acceptors are in particular the hydroxides of the alkali metals. For economic reasons, sodium hydroxide is generally preferred.

The reaction may be conveniently run from about 20° to about 50° C. and over a period of from about 50 to about 200 hrs. The reaction time depends upon the temperature at which the reaction is carried out and also on the amount of catalyst used.

The solvent used in this reaction can be selected from suitable aromatic hydrocarbons, such as benzene, toluene, xylene, o-dichlorobenzene and chlorinated aliphatic hydrocarbons such as methylene chloride. Toluene and methylene chloride are preferred.

The following examples are intended for purposes of illustration only and should not be interpreted as limiting the scope of the invention.

EXAMPLES 1 and 2 show the comparison of benzyltrimethylammonium chloride (BTEAC) and tetrabutylammonium hydrogen sulfate (TBAHS) in alkylation of azacycloheptan-2-one and azacyclononan-2-one with 1-bromododecane.

EXAMPLE 1

Preparation of 1-dodecylazacycloheptan-2-one using benzyltrimethylammonium chloride (BTEAC) and tetrabutylammonium hydrogen sulfate (TBAHS) as catalysts:

Four identical experiments were set up as follows. To a solution of 2.5 g (22.09 millimole) of azacycloheptan-2-one and 10 ml (41.64 millimole) of 1-bromododecane in 50 ml of toluene was added 50 ml of 50% sodium hydroxide solution. 1.1 millimole (0.05 mole %) of the catalyst (see table 1) was added. The heterogeneous mixture was vigorously stirred with a mechanical stirrer at 40°-50° C. for a specific reaction time (see table 1). The reaction mixture was then cooled to room temperature, the organic layer was separated, the aqueous layer was extracted with 2×100 ml of ether and the combined organic solution was washed twice with a saturated sodium chloride solution. After drying over anhydrous magnesium sulfate the filtrate was concentrated and the residue was fractionally distilled. The results are shown in Table 2 and clearly indicate the superiority of TBAHS over BTEAC as a catalyst for alkylation of lactams.

TABLE 1

Comparison of catalysts Benzyltrimethylammonium hydroxide (BTEAC) and Tetrabutylammonium hydrogen sulfate (TBAHS) in alkylation of Azacycloheptan-2-one with 1-Bromododecane.

| Experiment | 1 | 2 | 3 | 4 |
|---|---|---|---|---|
| Catalyst | BTEAC | TBAHS | BTEAC | TBAHS |
| Amount of Catalyst* (g) | 0.25 | 0.37 | 0.25 | 0.37 |
| Reaction Time (hrs.) | 30 | 30 | 114 | 114 |
| Starting Materials recovered in grams | 9.10 | 5.12 | 7.46 | 3.82 |
| Product isolated (g) | 0.5 | 4.78 | 1.39 | 5.66 |
| % yield | <8 | 77 | 22.5 | 91.3 |

*equivalent to 1.1 millimole

EXAMPLE 2

Preparation of 1-dodecylazacyclononan-2-one using benzyltrimethylammonium chloride (BTEAC) and tetrabutylammonium hydrogen sulfate (TBAHS) as catalysts:

Two identical experiments were set up as follows. To a solution of 2.5 g (17.7 millimole) of azacyclononan-2-one and 10 ml. (41.64 millimole) of 1-bromododecane in 50 ml. of toluene was added 50 ml. of 50% sodium hydroxide solution. 0.37 g of each catalyst was then added and the reaction mixture was vigorously stirred with a mechanical stirrer for 50 hrs. at 40°-50° C. After cooling to room temperature the reaction mixture was worked up as in EXAMPLE 1. the residue was fractionally distilled and the results are tabulated in Table 3.

TABLE 3

Comparison of catalysts Benzyltrimethylammonium chloride (BTEAC) and Tetrabutylammonium hydrogen sulfate (TBAHS) in alkylation of Azacyclononan-2-one with 1-Bromododecane.

| Catalyst | BTEAC | TBAHS |
|---|---|---|
| Amount in g | 0.37 | 0.37 |
| Millimoles | 1.62 | 1.1 |
| Reaction time (hrs) | 50 | 50 |
| Starting Materials recovered (g) | 9.57 | 6.0 |

TABLE 3-continued

Comparison of catalysts Benzyltrimethylammonium chloride (BTEAC) and Tetrabutylammonium hydrogen sulfate (TBAHS) in alkylation of Azacyclononan-2-one with 1-Bromododecane.

| Catalyst | BTEAC | TBAHS |
|---|---|---|
| Product isolated (g) | 0.79 | 4.10 |
| % Yield | 14 | 75 |

EXAMPLES 3-6 show the effect of other members of the claimed class of catalysts in alkylation of azacycloalkan-2-ones.

EXAMPLE 3

Preparation of 1-dodecylazacycloheptan-2-one with tricaprylylmethylammonium chloride (aliquat 336®) as catalyst.

To a solution of 2.5 g (22.09 millimole) of azacycloheptan-2-one and 10 ml (41.64 millimole) of 1-bromododecane in 50 ml of toluene was added 50 ml of 50% sodium hydroxide solution followed by 0.45 g (1.1 millimole) (0.05 mole %) of tricaprylylmethylammonium chloride (Aliquat 336®). The mixture was vigorously stirred with a mechanical stirrer at 40°-50° C. for 120 hrs. After cooling to room temperature the organic layer was separated, the aqueous layer was extracted with 2×100 ml of ether and the combined organic solution was washed twice with a saturated sodium chloride solution. After drying over anhydrous magnesium sulfate the filtrate was concentrated and the residue was fractionally distilled. 3.62 g forerun was excess 1-bromododecane (which can be recycled). The desired compound, 1-dodecylazacycloheptan-2-one distilled at 145°-155°/0.2 mm. Yield 6.15 g (99.2%).

EXAMPLE 4

Preparation of 1-dodecylazacycloheptan-2-one with TBAHS as catalyst.

EXAMPLE 3 was repeated on the same scale under identical conditions with 0.37 g (1.1 millimole) (0.05 mole %) of tetrabutylammonium hydrogen sulfate (TBAHS). After 160 hrs. the reaction was worked up as in EXAMPLE 3 and fractional distillation gave 6.0 g (96.8%) of 1-dodecylazacycloheptan-2-one.

EXAMPLE 5

Preparation of 1-dodecylazacycloheptan-1-one with THAC as catalyst.

EXAMPLE 3 was repeated on the same scale under identical conditions with 0.49 g (1.1 millimole) (0.05 mole %) of tetraheptylammonium chloride (THAC). After 120 hrs. the reaction was worked up as in EXAMPLE 3 Fractional distillation gave 6.0 g (96.8%) of 1-dodecylazacycloheptan-2-one.

EXAMPLE 6

Preparation of 1-dodecylazacycloheptan-2-one with DDMAB as catalyst.

EXAMPLE 3 was repeated on the same scale under identical conditions with 0.5 g (1.1 millimole) (0.05 mole %) of didodecyldimethylammonium bromide (DDMAB). After 120 hrs. the reaction was worked up as in EXAMPLE 3. Fractional distillation gave 5.74 g (92.5%) of 1-dodecylazacycloheptan-2-one.

We claim:

1. The method of synthesis of 1-dodecylazacycloheptan-2-one comprising reacting under aqueous conditions azacycloheptan-2-one with 1-bromo-dodecane in the presence of a catalytic amount of tricaprylylmethylammonium chloride.

2. The method of synthesis of 1-dodecylazacycloheptan-2-one comprising reacting under aqueous conditions azacycloheptan-2-one with a dodecyl-containing alkylating agent in the presence of a phase transfer catalyst selected from the group consisting of tricaprylylmethylammonium chloride tetrabutylammonium hydrogen sulfate, tetraheptylammonium chloride and didodecyldimethylammonium bromide.

3. The method of claim 2 wherein the dodecyl- containing alkylating agent is 1-halo-dodecane.

4. The method of claim 2 wherein the phase transfer catalyst is tricaprylylmethylammonium chloride.

* * * * *